United States Patent [19]

Epstein et al.

[11] 4,256,664

[45] * Mar. 17, 1981

[54] SUBSTANTIVE SUNSCREEN AGENTS

[75] Inventors: Morton B. Epstein, Chicago, Ill.; John F. Gerecht, Somerville, N.J.

[73] Assignee: Colgate-Palmolive Company, New York, N.Y.

[*] Notice: The portion of the term of this patent subsequent to Apr. 14, 1987, has been disclaimed.

[21] Appl. No.: 662,789

[22] Filed: Mar. 1, 1976

Related U.S. Application Data

[60] Continuation of Ser. No. 339,974, Mar. 12, 1973, abandoned, Division of Ser. No. 130,533, Apr. 1, 1971, abandoned.

[51] Int. Cl.$^3$ .................. C07C 103/19; C07C 103/26; A61K 7/44
[52] U.S. Cl. ..................................... 564/177; 424/59; 424/60; 424/324; 564/163; 564/166
[58] Field of Search .............. 260/558, 558 A, 558 R, 260/559 S; 424/59, 60, 324

[56] References Cited

U.S. PATENT DOCUMENTS

| | | | |
|---|---|---|---|
| 1,358,750 | 11/1920 | Kamm et al. | 260/472 |
| 1,513,730 | 11/1924 | Adams et al. | 260/472 |
| 1,596,259 | 8/1926 | Thayer | 260/472 |
| 1,676,470 | 7/1928 | Adams et al. | 260/472 |
| 2,175,782 | 10/1939 | Reever | 260/472 |
| 2,313,016 | 3/1943 | Horenstein et al. | 260/472 |
| 2,617,824 | 11/1952 | Moore et al. | 260/558 A |
| 2,668,100 | 2/1954 | Lurisi | 260/309.6 |
| 2,816,080 | 12/1957 | Chao | 260/309.6 |
| 2,935,525 | 5/1960 | Debus | 260/472 |
| 2,944,061 | 7/1960 | Jacob et al. | 260/309 |
| 3,002,886 | 10/1961 | Halpern | 260/501.15 |
| 3,069,321 | 12/1962 | Broh-Kahn et al. | 424/230 |
| 3,141,035 | 7/1964 | Lorz et al. | 260/501.15 |
| 3,506,758 | 4/1970 | Epstein et al. | 424/60 |

FOREIGN PATENT DOCUMENTS

| | | | |
|---|---|---|---|
| 399486 | 9/1965 | Switzerland | 260/559 |
| 862721 | 3/1961 | United Kingdom | 260/559 |

OTHER PUBLICATIONS

Machon, Chem. Abst., vol. 65, col. 2167–2168 (1966).
Herr et al., Chem. Abst., vol. 47, col. 8253 (1953).
Beltzly et al., JAC Soc., vol. 62, p. 2231 (1942).
Jensen et al., Acta. Chem. Scand., vol. 2, pp. 381–383 (1948).

*Primary Examiner*—Dale R. Ore
*Attorney, Agent, or Firm*—Herbert S. Sylvester; Murray M. Grill; Norman Blumenkopf

[57] ABSTRACT

Substantive sunscreen agents which are neutralized or quaternary ammonium salts of esters or amides of p-aminobenzoic acid, p-nitrobenzoic acid or salicylic acid with choline, lecithin, hydroxyalkyl-substituted imidazoles, 2,2-dialkylamino alkanols or alkylamines, pyridinesulfonamide, or colaminomethylformyl chloride, or omega halogenoalkylethers of salicylic acid quaternized with tertiary amines.

4 Claims, No Drawings

SUBSTANTIVE SUNSCREEN AGENTS

This is a continuation of application Ser. No. 339,974 filed Mar. 12, 1973, which is a divisional application of Ser. No. 130,533, filed Apr. 1, 1971, both now abandoned.

The present invention relates to sunscreening agents and more particularly to sunscreening agents having improved adhesion to the skin.

Contrary to common belief the benefits of exposing the human body to sunlight are more psychological than physiological. Although a suntanned body is admired as synonymous with good health in this part of the world, it is probably more a status symbol than a sign of physical fitness. It is said that in tropical agricultural countries where the working class must expose itself to the sun, a milk white skin rather than a "healthy tan" is considered desirable. Furthermore, reports on the harmful effects of sunlight on human skin have appeared in the medical literature. In a report of the Committee on Cosmetics to the American Medical Society [J. Am. Med. Assn. 161 1480-3 (1956); B. M. Kesten J. Am. Med. Assn. 161 1565-7 (1956)], these effects are reported. Chronic exposure to sunlight is considered by Knox et al. [J. M. Knox, J. Guin, and E. G. Cockerell J. Invest. Dermatology 29 435-44 (1957); J. M. Knox Am. Perfumer Aromat. 75 No. 8 42-4 (1960); J. M. Knox, A. C. Griffin, and R. E. Hakin J. Invest. Dermatology 34 51 (1960); J. M. Knox J. Soc. Cosmetic Chem. 13 119-24 (1962)] to be one of the major factors in the production of both cancerous conditions of the skin and the visible degenerative changes that occur with aging. Through Consumer Reports (Consumer Reports 1961 p. 397) the general public have been warned of the dangers of sunbathing.

The tanning of the skin when exposed to sunlight is part of nature's method of protecting the individual from the harmful effects of ultraviolet radiation including sunburn. Tanning is a result of several processes which are not well understood. Rothman [S. Rothman Physiology and Biochemistry of the Skin U. of Chicago Press p. 552 (1954)] indicates that formation of new melanin, brownish pigment of the skin, migration of new melanin to the surface and oxidative darkening of preformed melanin all play a role. The former process is said to be brought about by the erythema-producing radiation having a wave length between 2800 and 3100 A and the latter darkening produced by radiation between 3000 and 4200 A with a maximum effect as 3400 A. The necessity of erythemal radiation for new malanin formation has been questioned in recent reports [(a) M. A. Pathak, F. C. Riley, T. B. Fitzpatrick, and W. L. Curwen Nature 193 148-50 (1962) (b) M. A. Pathak, F. C. Riley, and T. B. Fitzpatrick J. Invest Parmatology 39 435-43 (1962)], and evidence is presented to indicate that melanin formation also is induced by long wave ultraviolet and even visible light.

The chemical structure of melanin is not known but is formed by the oxidation of tyrosine catalyzed by the enzyme tyrosinase probably via the following sequence:

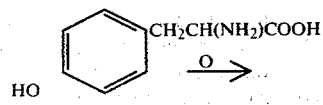

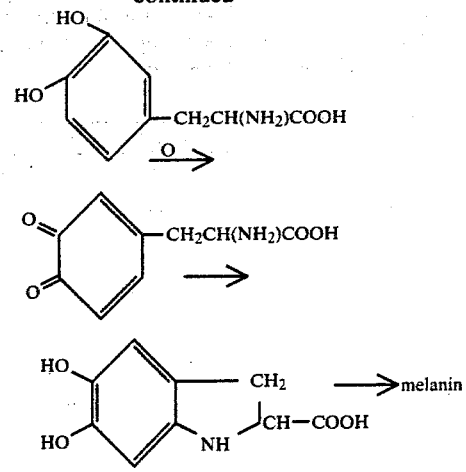

[(a) L. F. and M. Fieser Advanced Organic Chemistry Reinhold p. 1065-7 (1961) (b) R. A. Nicolauo and M. Piattelli J. Polymer Science 58 1133-9 (1962)].

The outer horny layer of the skin, the stratum corneum, also thickens after exposure to sunlight. This layer is highly ultraviolet absorbing and is thought to offer considerable protection to the ultraviolet sensitive lower layers of the skin [B. M. Kesten J. Am. Med. Assn. 161 1565-7 (1956)].

In addition, human perspiration contains urocanic acid,

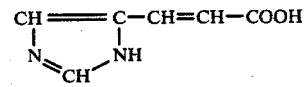

which is claimed to be a naturally occurring sunscreen. This compound shows an ultraviolet absorption between 2500 and 3000 A, the erythemal range, and is slated to be a natural defense against sunlight [(a) I. M. Hais and A. Zenisek Am. Perfumer and Aromat. 74 Sept. 1959 p. 26-8 (b) A. Zenisek, J. A. Kral and I. M. Hais Biochem. Biophysica Acta 18 589 (1955)].

"Sunscreens," synthetic compounds that absorb strongly in the ultraviolet region of the spectrum, have found wide use as protective agents against sunburn or erythema. Of the many compounds which have been tried over the years [E. G. Klarmann Am. Perf. and Essential Oil Rev. 58 33-8 126-35 (1949)] derivatives of salicyclic acid, p-aminobenzoic acid, 2-hydroxybenzophenone and 2-hydroxyphenylbenzotriazole have emerged as the most desirable "sunscreen" from the practical as well as theoretical point of view. However, as yet, no product is available which through regular use would impart convenient and constant protection against the damaging effects of ultraviolet radiation.

At least as early as 1946 it was recognized that one of the deficiencies of then existing "sun-tan" lotions was failure to protect because the sunscreening agent was diluted or floated off by perspiration. Resistance to water or sweat can be imparted to a degree by incorporating water repellents or emollients in the formulations. However, for various purposes such as more than occasional use and for incorporation in a variety of products it is advantageous to have as an active agent or agents in a formulation materials which not only absorb erythemal radiation but also adhere strongly to the skin.

Many compounds capable of absorbing ultraviolet radiation have been described in the literature and recommended as sunscreening agents. Among those recommended are the following:

| TYPE | SPECIFIC FORM |
|---|---|
| Aminobenzoic acids | o- and p-aminobenzoates and anthranilates |
| Hydroxybenzoic acids | salicylates and tannates |
| Cinnamic acid | menthyl and benzyl esters |
| Coumarins | unbelliferones; quercetin; esculin; daphnin |
| Biphenyls | o- and p-dihydroxybiphenyl disulfonates |
| Naphthols | sulfonates and carboxylates |
| Benzothiazoles | condensations of aromatic aldehydes and aminothiophenol |
| Imidazoles | uric acid and histidine derivatives; urocanic acid |
| "Sulfa" drugs | N',N'-Dimethyl-$N^4$-sulfanilyl-sulfanilamide; $N^4$-sulfanilylsulfanilamide |
| Aromatic ketones | benzalacetone; butyl-cinnamyl pyruvate |
| Piperonals | |
| Benzophenones | Highly purified, light yellow, powdered benzophenones, e.g., 2,2'-dihydroxy-4,4'-dimethoxy-benzophenone |
| Hydrocarbons | stilbenes |
| | acetanilide |
| | Vitamin C |

Most of the foregoing and other materials having the capability of absorbing ultraviolet light have not proved satisfactory for use as sunscreen agents for one or more of the following reasons: cost, safety, discoloration of fabrics among others. Some are not sufficiently selective between erythemal and tanning radiation. In spite of the deficiencies of the presently recognized sunscreening agents the most widely used at the present time are derivatives of aminobenzoic acid, salicylic acid, and the substituted benzophenones marketed under the tradename, "Uvinul."

It is emphasized that the presently available derivatives of aminobenzoic acid and of salicylic acid are not substantive. That is to say the presently available derivatives of aminobenzoic acid and of salicylic acid fail to protect when subjected to perspiration or to contact with water. In contrast, it is the principal object of the present invention to provide sunscreening agents which do not fail when subjected to perspiration and/or contact with water. That is to say the present invention provides substantive sunscreening agents.

Accordingly, it is an object of the present invention to provide a substantive sunscreening agent comprising the product of the esterification of p-aminobenzole acid and/or salicylic acid with lecithins, and/or with choline, and/or with imidazoles having a reactive hydroxyl group, e.g.,

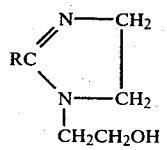

where R is hydrogen or alkyl. As those skilled in the art are aware lecithin and choline each have a quaternized nitrogen atom in the molecule. However, the imidazole esters are substantive only after they have been converted to a salt either through quaternization or neutralization with a suitable inorganic acid.

It is another object of the present invention to provide a substantive screening material comprising the product of the esterification of p-aminobenzoic acid and/or salicylic acid with imidazoles having a replaceable hydroxyl group followed by quaternization of the imidazole ring.

It is a further object of the present invention to provide a substantive sunscreening material comprising the product of the esterification of p-aminobenzoic acid and/or salicylic acid with 2,2-dialkylaminoalkanol preceded by or followed by quaternization, e.g., alkylation, benzylations, or carboxymethylation.

It is within the scope of the present invention to provide a substantive sunscreening material comprising the product of the ammonolysis of p-aminobenzoic acid and/or salicylic acid with an aliphatic diamine such as 3-dimethylamino-propylamine followed by quaternization.

The present invention also has as an object to provide a sunscreening material comprising -salicyl-, and/or -p-amino-benzoyl-, colaminomethylformylpyridinium chloride.

It is also within the scope of the objects of the present invention to provide a sunscreening material comprising the product of the quaternization of tertiary amines with betachloroethyl ether of salicylic acid or halogenoalkylethers of salicylic acid, including omega halogenoalkylethers of salicylic acid.

The present invention also has as an object to provide a substantive sunscreening material comprising the product of the quaternization of pyridinesulfonamides of p-aminobenzoic acid.

These and other objects of the present invention will become apparent to those skilled in the art from the following description of a substantive sunscreening material.

Salicylic acid per se is a good sunscreen agent but is not recommended for such use since it is a skin irritant. Methyl salicylate is also a sunscreening agent but is likewise a skin irritant. Homomenthyl salicylate is useful as a sunscreening agent and is not a strong skin irritant. However, homomenthal salicylate is not resistant to perspiration and contact with water.

In U.S. Pat. No. 2,128,334 a new class of compounds and their application to the absorption of light rays having wave lengths between 2900 and 3200 Angstrom units are disclosed. These compounds have the formula:

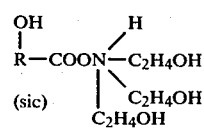
(sic)

R in the foregoing formula can be the benzene or the naphthalene nucleus and the hydroxyl group is ortho to the carboxyl group. In U.S. Pat. No. 2,260,173 among the media for protection from light disclosed therein is the ester of salicylic acid and an alcohol from the group consisting of lauryl and cetyl alcohols, octadecanol, cholesterol, and abietyl alcohol. N-salicyloyl-p-aminophenol is said to be mor effective than certain salicylates in U.S. Pat. No. 2,874,090. Thus, it is manifest that those skilled in the art have made many attempts to provide a more effective sunscreening agent by incorporating the salicyloyl radical in many organic compounds. However, there has been no suggestion that after quaternization the reaction product of an aliphatic diamine and salicylic acid is an effective substantive sunscreening agent.

The testing of compounds for substantivity to skin presents some problems. The most apparent difficulty is the limited availability of human skin. Hence, a material in relatively large supply is a necessary requirement when selecting a material for use as a substrate for controlled evaluation of the substantive as well as the sunscreening properties of the essential ingredient of a sunscreening composition. Human hair was selected as the test material for the following reasons:

1. It is readily available.
2. It bears a strong relation to the outer layer of skin, the stratum corneum; hydrogen bonds, salt linkages and Van der Wall's forces are considered to play similar roles in both hair and epidermal keratin [W. Montagna and R. A. Ellis The Biology of Hair Growth p. 147 Academic Press (1958)].
3. Although its protein structure is not completely known, it is much better characterized chemically than the stratum corneum.

PREPARATION OF HAIR

Approximately 50 gram hanks of untreated De Meo brown hair (from De Meo Brothers, New York City) were cut into ¼"-½" long clippings with an electric clipper. Each 50 gram hair batch was washed once with 2500 ml. of a 1.0 percent sodium bicarbnate solution by stirring vigorously for about two hours and then leaving it soak overnight. The sodium bicarbonate wash was then decanted and the hair was given six consecutive rinses with 2500 ml. portions of dionized water by stirring vigorously for ten minutes, settling for fifteen to twenty minutes and decanting. The sixth water rinse gave 97.5–99 percent light transmission in the 280–320 mu range determined with a Beckman DU quartz spectrophotometer. After decantation of the sixth water rinse, the hair was transferred to a Buchner funnel, broken up into small clumps or mats, and allowed to drain overnight. The bulk of the remaining surface water was removed by pressing the hair mats between paper towels. The last traces of surface water were removed by mechanically breaking down the hair mats into the individual fibers and blotting dry between sheets of filter paper. The hair was then transferred to a 66 percent humidity chamber, over saturated sodium nitrite solution, and conditioned for a minimum period of one week after which it was stored in a screw-capped glass jar until used.

METHOD OF MEASUREMENT

The standard procedure was to soak one gram samples of hair clippings (conditioned as described above) in a 10 ml. portion of a solution of the substantive agent in buffer and in a 10 ml. portion of the corresponding buffer (blank) for a period of exactly one hour. The solution and the buffer were then pipetted off of the hair samples and diluted with the original buffer. The solution was diluted to an appropriate concentration for ultra violet light (UV) absorption measurement and the buffer (blank) was diluted in the same proportion as the solution. UV absorption measurements were run on the diluted solutions and on an equivalent dilution of the original solution of substantive agent with the buffer using a Cary automatic recording spectrophotometer in the 250–350 mu range.

The Cary UV absorption curves continuously record the optical density (O. D.) of the solution, which is directly proportional to the amount of UV absorption at increasing wavelengths. The UV absorption by the solution of a material is directly proportional to the concentration. Pickup of the substantive agent by the hair lowers the concentration of materials in the solution resulting in a proportionate decrease in the O. D. The amount of substantive material picked up by the hair was calculated from the decreases in O. D. (at-peak absorption) resulting from contact with the hair corrected by the increase in O. D. of the corresponding buffer solution (blank) due to contact with the hair for the same length of time.

Illustrative of the preparation of a substantive sunscreening agent comprises ammonolysis of salicylic and/or p-amino-benzoic acids with an aliphatic diamine, e.g., 3-dimethylaminopropylamine to produce N-(3-dimethylaminopropyl) salicylamide hydrochloride. Preferably the N-(dialkylaminoalkyl) salicyl or p-aminobenzamide is quaternized.

N-(3-dimethylaminopropyl) salicylamide hydrochloride can be prepared in the following manner: Substantially equimolar amounts of methyl salicylate (0.20 mols, 30.4 parts by weight) and 3-dimethylaminopropylamine (0.20 mols, 20.4 parts by weight) are heated on a steam bath for at least about two hours. The resulting reaction mixture is dissolved in about fifty parts by weight of water and the pH of the solution adjusted to about five by the addition of hydrochloride acid. The water is removed by codistillation with toluene (volumetric ratio of toluene to solution being in the range of about one to one). Removal of the water leaves a syrupy hydrochloride which is substantially insoluble in toluene. This syrupy distillation residue is dissolved in about 100 milliliters of hot acetonitrile (volumetric ratio of acetonitrile to distillation bottoms about two to one). The acetonitrile solution of the syrupy distillation bottoms or residue is cooled to crystallize the reaction product. The crystals are separated from the mother liquor in any suitable manner as by suction on a Büchner funnel. The crystals are washed with acetonitrile and dried in air at about 50° C. The crystals had a melting point of 137°–140° C. and were recovered in a yield of 47 percent of theory. The crystals were analyzed for nitrogen and chlorine. N-(3-dimethylaminopropyl) salicylamide contains 10.83 percent of nitrogen and 13.73 percent of chlorine. The crystals were found to contain 10.64 percent of nitrogen and 13.76 percent of chlorine. From the following comparison of the calculated contents of nitrogen and chlorine and the concentration of nitrogen and chlorine in the product produced by the foregoing preparation it is manifest that the product is N-(3-dimethylaminopropyl) salicylamide hydrochloride

|  | Found | Calculated for |
|---|---|---|
| % Nitrogen | 10.64 | 10.83 |
| % Chlorine | 13.76 | 13.73 |

From the N-(3-dimethylaminopropyl) salicylamide hydrochloride a series of quaternary ammonium compounds can be prepared. Illustrative of these quaternary ammonium compounds of N-(3-dimethylaminopropyl) salicylamide is the dodecyl quaternary ammonium compound, 3-salicylamidopropyl dimethyl dodecyl ammonium bromide. To prepare 3-salicylamidopropyl-dimethyl dodecyl ammonium bromide the aforedescribed N-(3-dimethylamino-propyl) salicylamide hydrochloride is dissolved in isopropyl alcohol in the proportion of 0.04 mol in 30 milliliters of the isopropyl alcohol to which is added a stoichiometric equivalent of alkali metal hydroxide, preferably potassium or sodium hydroxide, dissolved in methanol. Thus, for example, to the solution of N-(3-dimethylaminopropyl) salicylamide hydrochloride 18.3 milliliters of 2.18 normal methanolic potassium hydroxide solution are added. The alkali metal halide formed in this example potassium chloride is separated from the reaction mixture in any suitable manner as by filtration. To the clear filtrate 0.048 mol of 1-bromododecane is added, the reaction mixture refluxed for about five to twenty-four hours and the solvent alcohols removed in any suitable manner as on a steam bath. The residue is crystallized from ethyl acetate.

The product is a white, crystalline powder having a melting point of 94° to 96° C. Upon analysis the product was found to contain 5.74 percent of nitrogen and 16.31 percent of bromine. For 3-salicylamidopropyl dimethyl dodecyl ammonium bromide monohydrate the corresponding values are 5.73 percent of nitrogen and 16.33 percent of bromine from which it is manifest that the product is 3-salicylamidopropyl dimethyl dodecyl ammonium bromide monohydrate.

The ultraviolet spectrum of 3-salicylamidopropyl-dimethyl-dodecyl-ammonium bromide and its adsorption on a proteinaceous material at different concentrations and acidities were determined. For the proteinaceous material human hair was used. The amount of the quaternary ammonium bromide adsorbed by the hair was measured by determining ultraviolet absorption spectra before and after one hour contact with the solution of the quaternary ammonium bromide. The acidity was controlled by using the buffer solutions as indicated hereinafter. The data obtained are presented in the following table:

TABLE I

| Run No. | pH | Initial Concentration of QAB[4] percent by weight | Ultraviolet Absorption Maximum Angstroms | Adsorption from 10 grams of solution of QAB[5] mg/gm of Hair | Percent of Available |
|---|---|---|---|---|---|
| 1 | 4.8[1] | 0.02 | 2980 | 1.68 | 83.9 |
| 2 | 7.1[2] | 0.02 | 3020 | 2.00 | 100.0 |
|   |   | 0.10 | 3050 | 7.23 | 72.3 |
| 3 | 8.5[3] | 0.02 | 3130 | 1.87 | 92.9 |

[1]0.1 molar sodium acetate - acetic acid
[2]0.058 molar triethanolamine hydrochloride
[3]0.13 molar sodium borate and 0.035 molar sodium chloride
[4]3-salicylamidopropyl-dimethyl-dodecyl-ammonium bromide
[5]milligrams of QAB per gram of hair Those skilled in the art will recognize from the foregoing data (1) that as the pH of the solution of QAB changes from acid through neutral to alkaline the maximum wave length of the light absorbed rises from 2980 Angstroms to 3130 Angstroms; (2) that the absolute amount of QAB absorbed is dependent upon the initial concentrations of QAB and (3) that the maximum efficiency of adsorption of QAB occurs when the solution of QAB is substantially neutral.

Similar experiments with cellulose and nylon fibers showed strong adsorption of the quaternary to these fibrous materials.

The substantive character of the novel sunscreening materials of the present invention or in other words the capability of the novel sunscreening materials of the present invention of providing adequate adhesion to the skin of a human, hair, proteins, cellulosic fibers, other fibers, glass and other materials and thus provide resistance to perspiration and water is made manifest by the following data:

A series of compounds were prepared which contained both salicylic acid and quaternary ammonium moieties in the same molecule. Readily available starting materials were used to prepare this series of 3-salicylamidopropyl dimethyl alkyl ammonium bromides by the following reaction sequence.

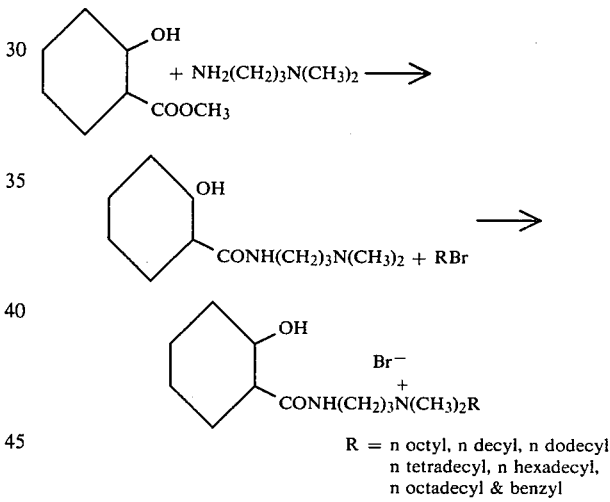

R = n octyl, n decyl, n dodecyl
n tetradecyl, n hexadecyl,
n octadecyl & benzyl

All of these compounds except the benzyl quaternary were obtained as hydrates.

Pick up by hair of some of these compounds (see Tables II and III) were studied. In general these compounds were strongly substantive to hair over a range of concentration and pH.

TABLE II

PICKUP OF QUATERNARIES BY HAIR FROM 0.02% SOLUTIONS IN BUFFERS AT VARIOUS pH VALUES

| MATERIAL | BUFFER[1] pH | WAVE LENGTH FOR MAXIMUM ABSORPTION Mu | MILLIGRAMS PICKED UP[2] PER GRAM OF HAIR | % PICKUP |
|---|---|---|---|---|
| p-Aminobenzoic Acid | 4.8 | 273 | 0.54 | 27.0 |
|  | 7.1 | 265 | 0.09 | 4.5 |
|  | 8.5 | 266 | Zero | Zero |
|  | 10.0 | 265 | Zero | Zero |

TABLE II-continued

PICKUP OF QUATERNARIES BY HAIR FROM 0.02% SOLUTIONS IN BUFFERS AT VARIOUS pH VALUES

| MATERIAL | BUFFER[1] pH | WAVE LENGTH FOR MAXIMUM ABSORPTION Mu | MILLIGRAMS PICKED UP[2] PER GRAM OF HAIR | % PICKUP |
|---|---|---|---|---|
| Salicylic Acid | 4.8 | 296 | 0.68 | 34.0 |
|  | 7.1 | 296 | 0.09 | 4.5 |
|  | 8.5 | 301 | Zero | Zero |
|  | 10.0 | 297 | Zero | Zero |
| N-(3-dimethylamino- | 4.8 | 297.5 | 0.15 | 7.5 |
| propyl) Salicylamide | 7.1 | 299.5 | 0.48 | 24.0 |
| —HCl | 8.5 | 309 | 0.16 | 8.0 |
|  | 10.0 | 325 | 0.01 | 0.5 |
| 3-Salicylamidopropyl | 4.8 | 298 | 0.32 | 16.0 |
| dimethyl benzyl | 7.1 | 300 | 0.81 | 40.5 |
| Ammonium Chloride | 7.1[3] | 301 | 0.97 | 48.5 |
|  | 8.5 | 312 | 0.35 | 17.5 |
|  | 10.0 | 326.5 | 0.06 | 3.0 |
| 3-Salicylamidopropyl | 4.8 | 298 | 1.68 | 84.0 |
| dimethyl lauryl | 7.1[3] | 302 | 2.00 | 100.0 |
| Ammonium Bromide | 8.5 | 313 | 1.86 | 93.0 |
| 3-Salicylamidopropyl dimethyl allyl Ammonium Chloride | 7.1[3] | 300 | 0.52 | 26.0 |
| 3-Salicylamidopropyl dimethyl butyl Ammonium Bromide | 7.1[3] | 300 | 0.57 | 28.5 |

[1]pH = 4.8–0.1 and 1.0 molar acetate - acetic acid buffer
pH = 7.1–0.067 molar phosphate buffer
pH = 8.5–0.13 molar borate + 0.035 molar NaCl
pH = 10.0–0.116 molar borate buffer
[2]Total amount of material available = 2.0 mgs.
[3]0.058 and 0.064 molar triethanolamine . HCl buffer

TABLE III

PICKUP OF 3-SALICYLAMIDOPROPYL DIMETHYL ALKYL AMMONIUM COMPOUNDS BY HAIR AS A FUNCTION OF SOLUTION CONCENTRATIOn AT pH = 7.1 (0.065) MOLAR TRIETHANOLAMINE - HCl BUFFER

| ALKYL = | CONCENTRATION GS/100 ML | AVAILABLE MATERIAL MGS. | WAVE LENGTH FOR MAXIMUM ABSORPTION Mu | MILLIGRAMS PICKED UP PER GRAM OF HAIR | % PICKUP |
|---|---|---|---|---|---|
| Octyl ($C_8$) | 0.10 | 10 | 300.5 | 5.37 | 53.7 |
|  | 0.17 | 17 | 301 | 7.63 | 44.9 |
|  | 0.35 | 35 | 300.5 | 11.27 | 32.2 |
|  | 0.35 | 35 | 300.5 | 10.78 | 30.8 |
|  | 0.35 | 35 | 300 | 9.49 | 27.1 |
|  | 0.35 | 35 | 300 | 9.77 | 27.9 |
|  | 0.50 | 50 | 300.5 | 12.35 | 24.7 |
| Decyl ($C_{10}$) | 0.10 | 10 | 300 | 7.36 | 73.6 |
|  | 0.17 | 17 | 301 | 9.30 | 54.7 |
|  | 0.35 | 35 | 300.5 | 9.66 | 27.6[1] |
| Lauryl ($C_{12}$) | 0.02 | 2 | 302 | 2.00 | 100.0 |
|  | 0.10 | 10 | 305 | 7.23 | 72.3 |
|  | 0.17 | 17 | 306 | 8.06 | 47.4[1] |

[1]Probably low due to noticeable turbidity

The substantive character of the hereinbefore described class of sunscreening agents in contrast to the non-substantive character of prior art sunscreening agents was determined in a "go-nogo" qualitative manner. Four sunscreening agents were prepared as follows:

(1) A widely advertised liquid oil-base preparation having as its predominant sunscreening agent homomenthyl salicylate.

(2) A 10 percent solution of homomenthyl salicylate in isopropanol.

(3) A 10 percent solution of 3-salicylamide-propyl-dimethyl-dodecyl-ammonium bromide in a mixture of isopropanol and water containing 50 percent of isopropanol and 50 percent of water.

(4) A 10 percent solution of 3-salicylamidopropyl-dimethyl-octadecyl-ammonium bromide in a mixture of isopropanol and water containing 50 percent of isopropanol and 50 percent of water.

To each finger of one hand of the investigator two drops of one of the aforedescribed sunscreening preparations were applied. Immediately after the sunscreening preparations applied to the fingers had dried, the fingers were observed under black light which causes certain materials which absorb ultraviolet light to fluoresce. (A Minerallight Ultraviolet Lamp, Short Wave Sl 2537 manufactured by Ultraviolet Products, Inc., San Gabriel, California was used.) All of the treated areas fluoresced strongly but with different colors. Thereafter, the hand was washed with toilet soap and water in the usual manner and dried by rubbing with a paper towel. The hand was again exposed to the black light. It was observed that the area to which the aforedescribed sunscreening agent (1) had been applied was practically free of fluorescence. The areas to which the aforedescribed sunscreening agents (3) and (4) had been applied were highly fluorescent. The area to which the aforedescribed sunscreening preparation (2) had been applied was less fluorescent than the areas to which preparations (3) and (4) had been applied. Subsequently, after several normal washings of the hand during the day the hand was again observed under the black light. It was observed that, after several normal and usual washings, with toilet soap and water, the area to which preparation (1) had been applied no longer exhibited any fluorescence; the area to which preparation (2) had been applied showed a slight fluorescence; in contrast to the foregoing, the areas to which sunscreening agents (3) and (4) had been applied still showed strong fluorescence. From which it follows that the sunscreening agents of the present invention are substantive and far more substantive than a sunscreening preparation which enjoys very wide consumer acceptance for the purpose.

Those skilled in the art will understand that capabilities of 3-salicylamidopropyl-dimethyl-dodecyl-ammonium bromide are illustrative of the capabilities to a greater or lesser degree of the novel substantive sunscreening agents of the present invention. These substantive sunscreening agents are derivatives of salicylic acid and p-aminobenzoic acid and have compositions represented by the general formula:

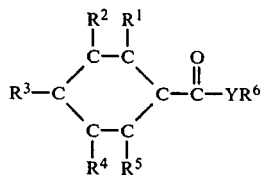

where $R^1$ is hydroxyl or hydrogen; $R^2$, $R^4$, and $R^5$ are hydrogen; $R^6$ is (A) the radical of lecithin, choline, imidazoles either quaternized or neutralized, (B) the radical 2,2-diethylaminoethyl alkylated, benzylated, carboxymethylated, or neutralized, (C) quaternized or neutralized aliphatic diamines, (D) colaminomethylformylpyridinium halide, (E) quaternized or neutralized tertiary amines, when $R^1$ is hydroxyl, $R^3$ is hydrogen, and when $R^1$ is hydrogen; $R^3$ is $HN_2$ or $NO_2$; and Y is —O— or NH.

While in the preparation of 3-salicylamidopropyl-dimethyl-dodecyl-ammonium bromide in the first step methyl salicylate was reacted with N-(3-dimethylaminopropylamine) those skilled in the art will understand that in the formula

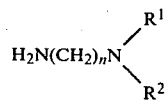

n is an integer 2 to 12 and $R^1$ and $R^2$ are the same or different alkyl groups having 1 to 5 carbon atoms.

Furthermore, the substituted aliphatic diamine can be reacted with p-amino- or p-nitro-benzoic acid rather than orthohydroxybenzoic acid or with a mixture of two or more of these substituted benzoic acids. In addition, these aromatic amides can be reacted with monohalogenated alkanes having four to eighteen carbon atoms or benzyl halides. The nitro compounds produced from the nitrobenzoic acid can be reduced by the usual procedure to the corresponding amino compounds. Accordingly, the generic formula of the sub-class of sunscreening agents used to illustrate the generic inventive concept is

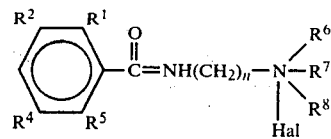

where
$R^2$, $R^4$, and $R^5$ are hydrogen
$R^1$ is hydroxyl (when $R^1$ is hydroxyl, $R^3$ is hydrogen).
$R^3$ is $NH_2$ or $NO_2$ (when $R^3$ is $NH_2$ or $NO_2$, $R^1$ is hydrogen).
n is an integer two to twelve.
$R^6$ is an alkyl group having one to five carbon atoms.
$R^7$ is an alkyl group having 1 to 5 carbon atoms.
$R^6$ and $R^7$ are the same or different alkyl groups.
$R^8$ is an alkyl group having three to eighteen carbon atoms or benzyl and Hal is bromine or chlorine Various 3-salicylamidopropyldimethylalkyl ammonium halides were produced following substantially the same procedure as was followed in preparing 3-salicylamidopropyldimethyldodecyl ammonium bromide described hereinbefore. The quaternary ammonium halides and the analyses for water and halogen are presented in the following tabulation.

TABLE IV

ANALYSIS - 3-SALICYLAMIDOPROPYL DIMETHYL ALKYL AMMONIUM HALIDES

| R | X | Equiv.[1] Found | % $H_2O$[2] | Calc. Equiv.[3] | Moles $H_2O$[4] Mole Comp. |
|---|---|---|---|---|---|
| n Octyl | Br | 437 | 4.03 | 432.9 | 0.978 |
| n Decyl | Br | 459 | 1.28 | 448.7 | 0.326 |
| n Dodecyl | Br | 490 | 3.33 | 487.2 | 0.907 |
| n Tetradecyl | Br | 524 | 3.51 | 517.2 | 1.022 |
| n Hexadecyl | Br | 549 | 2.91 | 542.9 | 0.888 |
| n Octadecyl | Br | 575 | 3.04 | 573.4 | 0.971 |
| n Benzyl | Cl | 347 | — | 348.5 | — |

[1]Weight per halogen by potentrometric titration.
[2]By Karl Fisher
[3]These figures are corrected for water content found.
[4]Calculated from the found equiv. weight and the determined water content

What is claimed is:
1. A substantive sunscreening compound of the formula

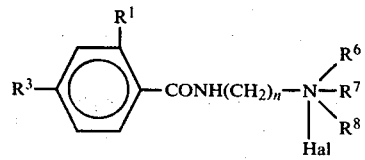

wherein:
$R^1$ is H or OH;
$R^3$ is $NH_2$ or $NO_2$ when $R^1$ is H and H when $R^1$ is OH;
$R^6$ and $R^7$ are each $C_{1-5}$ alkyl groups;
$R^8$ is $C_{8-18}$ alkyl;
n is an integer from 2 to 12; and
Hal is Cl or Br
2. A compound according to claim 1 wherein $R^1$ is OH.
3. A compound according to claim 2 wherein $R^6$ and $R^7$ are each $CH_3$ an n is 3.
4. A compound according to claim 3 wherein $R^8$ is dodecyl.

* * * * *